(12) United States Patent
Chevallet et al.

(10) Patent No.: US 6,684,710 B2
(45) Date of Patent: Feb. 3, 2004

(54) DEVICE FOR MEASURING PRESSURE COMPRISING A MEMBRANE MOULDED INTO A CASSETTE

(75) Inventors: Jacques Chevallet, Sérézin du Rhône (FR); Thierry Court, Villeurbanne (FR); Guy Mercier, Bron (FR)

(73) Assignee: Hospal International Marketing Management, Lyons (FR)

( * ) Notice: Subject to any disclaimer, the term of this patent is extended or adjusted under 35 U.S.C. 154(b) by 0 days.

(21) Appl. No.: 10/004,857

(22) Filed: Dec. 7, 2001

(65) Prior Publication Data

US 2002/0107468 A1 Aug. 8, 2002

(30) Foreign Application Priority Data

Dec. 8, 2000 (FR) .............................. 00 15968

(51) Int. Cl.⁷ ................................. G01L 9/00
(52) U.S. Cl. ...................................... 73/723
(58) Field of Search ................... 73/723, 715, 700, 73/1.57

(56) References Cited

U.S. PATENT DOCUMENTS

| | | | | |
|---|---|---|---|---|
| 4,657,490 A | * | 4/1987 | Abbott | 417/478 |
| 4,951,509 A | * | 8/1990 | Yamauchi | 73/730 |
| 5,098,262 A | * | 3/1992 | Wecker et al. | 417/479 |
| 5,108,367 A | * | 4/1992 | Epstein et al. | 604/67 |
| 5,215,450 A | | 6/1993 | Tamari | |
| 5,392,653 A | | 2/1995 | Zanger et al. | |
| 5,399,171 A | | 3/1995 | Bowman et al. | |
| 5,429,485 A | * | 7/1995 | Dodge | 417/442 |
| 5,588,816 A | * | 12/1996 | Abbott et al. | 417/479 |

FOREIGN PATENT DOCUMENTS

WO   WO 99/13926   3/1999

* cited by examiner

*Primary Examiner*—Edward Lefkowitz
*Assistant Examiner*—Andre Allen
(74) *Attorney, Agent, or Firm*—Young & Thompson

(57) ABSTRACT

The invention proposes a device for measuring the pressure of blood in a pipe (44) of an extracorporeal blood circuit (42) includes a pressure measurement section (46) having a substantially rigid wall (64) including a hole (66) which is sealed by a closure element (68), the internal face (70) of which is in contact with the blood and the external face (72) of which is in contact with the ambient air, it being possible for the closure element (68) to be elastically deformed overall along a deformation axis (A—A) under the effect of the blood pressure. The closure element (68) is made in a single piece with the associated rigid wall (64) of the pressure measurement section (46).

16 Claims, 3 Drawing Sheets

DEVICE FOR MEASURING PRESSURE COMPRISING A MEMBRANE MOULDED INTO A CASSETTE

FIELD OF THE INVENTION

The present invention relates to a device for measuring the pressure of blood.

More particularly, the present invention relates to a device for measuring the pressure of blood, which is used in an extra corporeal blood treatment device in which the blood is taken from a patient in order to be treated then reintroduced into the body of the patient (especially for the purpose of carrying out dialysis) by means of an extracorporeal blood circuit comprising pipes and including at least one section for measuring the pressure of blood flowing in a pipe.

BACKGROUND OF THE INVENTION

A known type of pressure measurement section comprises, in a substantially rigid wall, a hole which is sealed by a closure element, the internal face of which is in contact with the blood and the external face of which is in contact with the ambient air, it being possible to elastically deform or displace the closure element overall along a deformation or displacement axis which is substantially orthogonal to its general plane, under the effect of the blood pressure; a portion of the external face of the closure element, in its rest state, is in direct or indirect contact with a load sensor which can measure the force applied axially to the internal face of the closure element by the pressure of the blood, in order to calculate therefrom the value of this pressure.

Generally, this type of extracorporeal blood treatment device comprises a circuit part which is made from a casing, or cassette, of the disposable type, incorporating pipes which are connected to the extracorporeal blood circuit.

The pressure measurement section may be an attached module which is mounted in an associated housing of the casing.

The casing is mounted on a support apparatus which comprises, for example, sensors, display means, pumping means, a control interface, an electronic control unit, etc.

In this type of extracorporeal blood treatment device, the blood pressure must be measured without contact between the measurement member and the blood.

Several systems for carrying out this pressure measurement are known.

In a first pressure measurement system, which is shown in FIG. 1, a pressure measurement section 10 in a pipe 12 comprises a measurement chamber 14 in which a membrane 16, or diaphragm, separates the blood flowing in the pipe 12 from the air contained in a compartment 18.

The membrane 16 can be deformed along a deformation axis A—A which is orthogonal to its general plane, so that it is displaced axially according to the pressure of the blood in the pipe 12.

The extreme deformation positions of the membrane 16 are shown by dotted lines.

The air compartment 18 is sealed shut when the pressure measurement section 10 is mounted on a support apparatus 20.

The support apparatus 20 comprises a sensor 22 which directly measures the pressure in the air compartment 18.

When the blood pressure changes, the membrane 16 is axially displaced to an equilibrium position in which the pressure on both sides of the membrane 16 is equal.

The pressure measured by the sensor 22 in the air compartment 18 is therefore equal to the pressure of the blood in the pipe 12.

By virtue of a suitable geometry, in particular by virtue of a suitable volume for the compartment 18 and a suitable surface-area for the membrane 16, this first pressure measurement system makes it possible to measure, on the one hand, so-called "positive" blood pressures, that is to say, blood pressures which are greater than a reference pressure, in this case atmospheric pressure, and, on the other hand, so-called "negative" blood pressures, that is to say blood pressures which are less than the reference pressure.

This measurement system operates correctly provided that there are no leaks in the air compartment 18, otherwise the membrane 16 is displaced right up to its end stop and it no longer carries out the function of transmitting pressure.

The seal of the air compartment 18 during mounting of the pressure measurement section 10 on the support apparatus 20, is a weak point of the measurement system.

In particular, the seal may be impaired during use of the measurement system.

In a second pressure measurement system, which is shown in FIG. 2, the pressure measurement section 10 forms a compartment 24 containing the blood and one wall 26 of which comprises a hole 28 which is sealed by a flexible membrane 30.

When the pressure measurement section 10 is mounted on the support apparatus 20, the external face of the central part of the flexible membrane 30 is in contact with a load transmitter 32 which is inserted between the membrane 30 and a load sensor 34.

The load sensor 34 makes it possible to measure the forces applied to the internal face of the membrane 30 because of the effect of the blood pressure in the compartment 24, where the blood pressure is greater than the ambient air pressure.

The blood pressure is determined by the equation:

$$P = \frac{F - F_0}{S_a} \quad (1)$$

In this equation, F is the force measured by the load sensor 34, $F_0$ is the force measured in the rest state, that is to say, in the absence of a pressure gradient between the two sides (internal and external faces) of the membrane 30, and $S_a$ is the active area or active surface area of the membrane 30.

The active surface area $S_a$ of the membrane 30 is equivalent to an area intermediate between the total area of the internal face of the membrane 30 in contact with the blood and the area of contact between the membrane 30 and the load transmitter 32.

This measurement system allows positive pressures to be measured but it does not allow negative pressures to be measured.

This is because, for negative pressures, the membrane 30 tends to come away from the load transmitter 32. The load sensor 34 can then no longer measure the forces which are applied to the membrane 30.

This system has therefore been adapted to measure negative pressure.

In order that the load sensor 34 can continue to measure the forces which are applied to the membrane 30, when the blood pressure is negative, the membrane 30 is secured in axial displacement to the load transmitter 32.

Thus, according to one improved embodiment of the second pressure measurement system, which is shown in FIG. 3, the membrane has a metal disc 36 on its external face and the load transmitter 32 has a magnet 38 at its axial end facing the membrane 30.

The magnetic attraction exerted by the magnet 38 on the metal disc 36 makes it possible to secure the membrane 30 in axial displacement to the load transmitter 32.

When the pressure is positive, the membrane 30 exerts a force which pushes axially against the load transmitter 32.

When the pressure is negative, the membrane 30 exerts a force which axially pulls the load transmitter 32.

This device for securing the membrane 30 to the load transmitter 32 is expensive since it requires a special membrane 30 fitted with a metal disc 36 and a special load transmitter 32 fitted with a magnet 38.

The metal disc 36 must have a large area in order to allow effective magnetic coupling.

In addition, the membrane 30 is subject to a significant jolt when the metal disc 36 "sticks" to the magnet 38 of the load transmitter 32, which may impair its mechanical characteristics.

Moreover, it is noted that the known measurement systems require an attached membrane 30, which is made from a material different to that of the pressure measurement section 10.

The two pressure measurement systems generally use flexible membranes 30 made of silicone.

An attached membrane 30 is relatively complex to mount since the membranes 30 must completely seal the hole 28 of the associated wall 26, which involves high manufacturing and assembly costs for the pressure measurement system.

SUMMARY OF THE INVENTION

The purpose of the invention is to remedy these drawbacks and to provide a pressure measurement system which is simpler than the existing systems.

For this purpose, the invention proposes a device for measuring the pressure of blood in a pipe of an extracorporeal blood circuit, comprising a pressure measurement section having a substantially rigid wall including a hole which is sealed by a closure element, the internal face of which is in contact with the blood and the external face of which is in contact with the ambient air, it being possible for the closure element to be elastically deformed or displaced overall along a deformation or displacement axis which is substantially orthogonal to its general plane, under the effect of the blood pressure, the pressure measurement section being designed to engage with a load sensor so that a portion of the external face of the closure element is, in its rest state, in direct or indirect contact with a load sensor which can measure the force applied axially on the internal face of the closure element by the blood pressure, in order to calculate therefrom the value of this pressure, characterized in that the closure element is made in a single piece with the associated rigid wall of the pressure measurement section.

Other than its manufacturing cost, which is less than that of a flexible membrane attached to a pressure measurement section, the closure element according to the invention makes it possible to overcome specific problems connected with the use of flexible membranes.

To be precise, it has been observed that when a given sustained force is applied to a flexible silicone membrane, a phenomenon of creep appears, that is to say that there is a deterioration in the elastic properties of the membrane over time.

After a given period, the membrane therefore remains deformed in spite of a return to the initial conditions corresponding to its rest state.

This phenomenon of creep is particularly significant for large diameter membranes, that is to say membranes whose diameter is greater than 25 millimeters, made of silicone or of natural rubber, which lose about eight percent of their elasticity in one hour.

The temperature and the hydration of the membrane may also cause deterioration of its properties, particularly its elasticity.

According to other characteristics of the invention:

- the closure element includes a region of lower resistance to elastic axial deformation, compared to the rigid wall;
- the region of lower resistance to elastic axial deformation circumscribes the portion of the external face of the closure element which, in its rest state, is in direct or indirect contact with the load sensor;
- the closure element comprises a substantially rigid central pellet which is delimited by a thinned peripheral annular region of axial thickness less than the axial thickness of the rigid wall in order to form an elastically deformable region;
- the thinned region is made by machining the rigid wall associated with the closure element;
- the closure element is made by moulding with the associated rigid wall;
- in cross section on a plane which is substantially perpendicular to the general plane of the closure element, the profile of the thinned region is substantially undulating;
- a load transmitter is inserted axially between the external face of the closure element and the load sensor;
- the load sensor, or the load transmitter, applies an initial axial pretensioning force to the closure element, in its rest state, for the purpose of making it possible, in particular, to measure a pressure less than the pressure of the ambient air or to measure a reduction in pressure with respect to a reference pressure;
- the external face of the closure element comprises a gripping member, or a member that can be gripped, which engages with a complementary member of the load transmitter, so as to secure the closure element in axial displacement with the load transmitter, for the purpose of making it possible, in particular, to measure a pressure less than the pressure of the ambient air or to measure a reduction in pressure with respect to a reference pressure;
- the gripping member, or the member which can be gripped, of the closure element is made in a single piece with the pellet;
- when a part of the circuit is made up of a casing, or cassette, incorporating pipes which are connected to the extracorporeal blood circuit, the pressure measurement section is an attached module which is mounted in an associated housing of the casing;
- when a part of the circuit is made up of a casing, or cassette, incorporating pipes which are connected to the extracorporeal blood circuit, the pressure measurement section is moulded into the casing;
- the closure element is substantially disc-shaped;
- at least one portion of the rigid wall bordering the hole bears axially towards the outside against a support plate.

BRIEF DESCRIPTION OF THE DRAWINGS

Other characteristics and advantages of the invention will appear on reading the following detailed description, for the understanding of which, reference may be made to the appended drawings in which.

DETAILED DESCRIPTION OF THE INVENTION

In the following description, identical or similar elements will be denoted by identical references.

Figure 1:
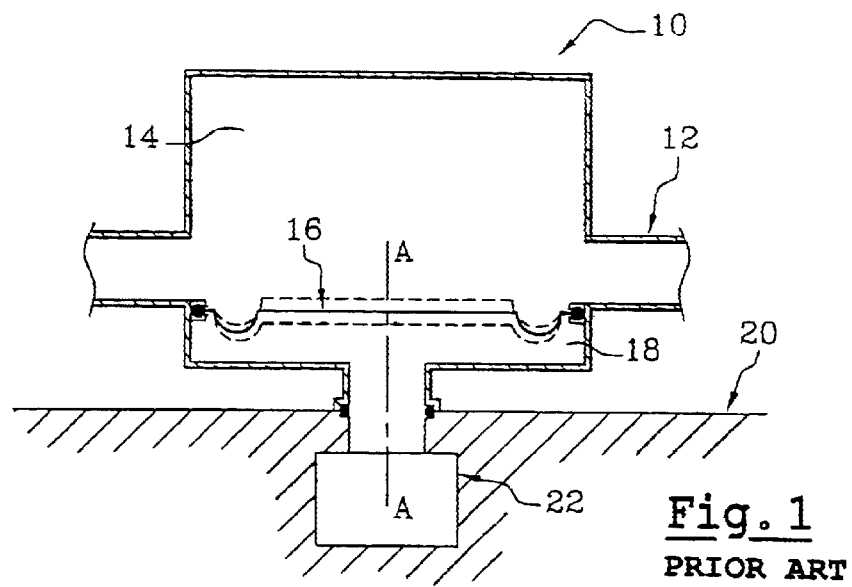
FIG. 1 is a schematic view in cross section which shows a first type of pressure measurement system according to the prior art.
Figure 2:
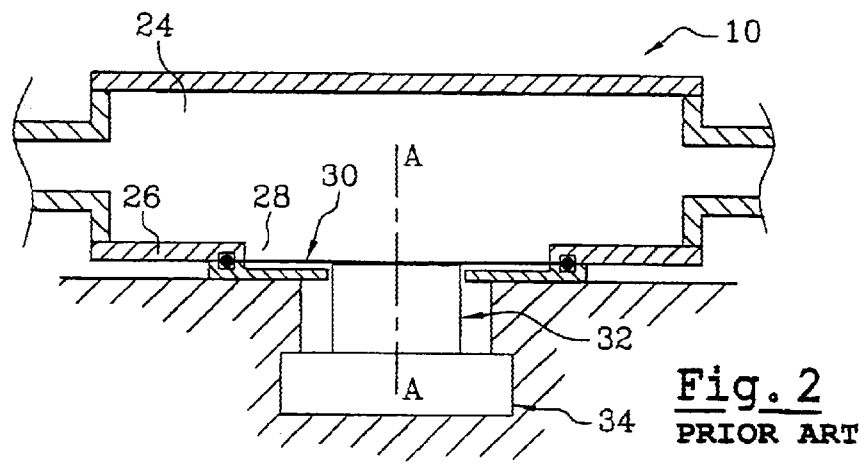
FIG. 2 is similar to that of FIG. 1 which shows a second type of pressure measurement system according to the prior art.
Figure 3:
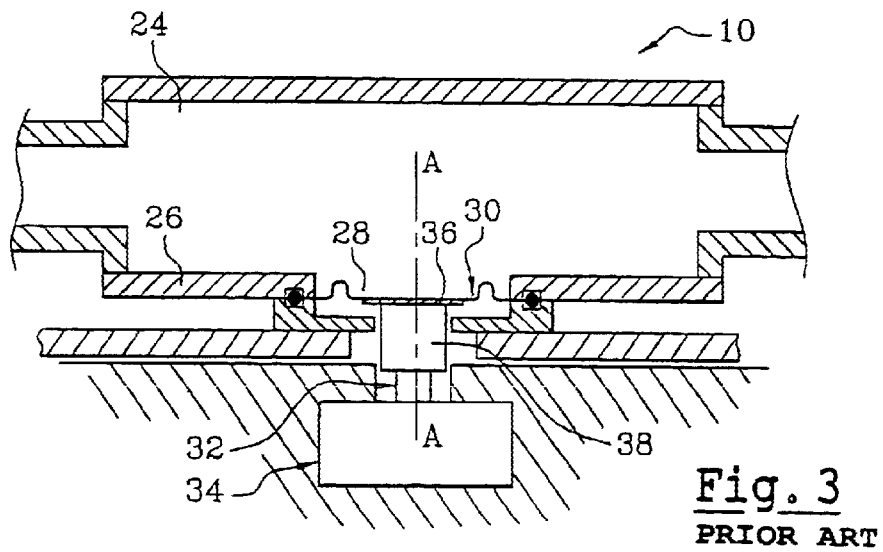
FIG. 3 is a view similar to that of FIG. 1 which shows an improvement to the pressure measurement system of FIG. 2 according to the prior art.
Figure 4:
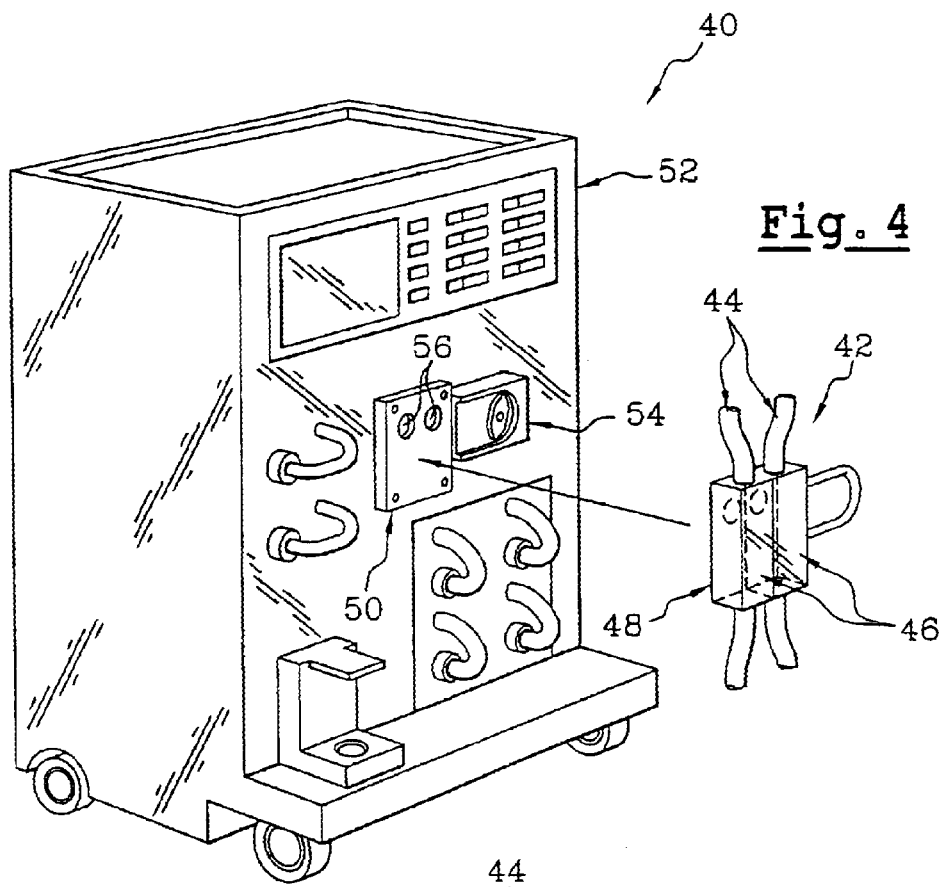
FIG. 4 is a perspective view which shows schematically an extracorporeal blood treatment device made according to the teachings of the invention.

FIG. 4 shows an extracorporeal blood treatment device 40 for the purpose of carrying out dialysis.

This device 40 is designed to take blood from a patient, to treat it for the purpose of carrying out dialysis, then to reintroduce it into the body of the patient.

This device 40 comprises an extracorporeal blood circuit 42 (shown partially here) comprising pipes 44 and including at least one section 46 for measuring the pressure of the blood flowing in a pipe 44.

In this case, part of the extracorporeal blood circuit 42 is made up of a substantially parallelepipedal casing 48, also called a cassette, which, in its thickness, contains pipes 44 for the flow of blood, which, in its thickness are connected to the other pipes 44 of the extracorporeal blood circuit 42.

In this case, the cassette 48 comprises two similar pressure measurement sections 46 which are contained in its thickness.

The cassette 48 is designed to be mounted on a support plate 50 of a dialysis apparatus 52, which comprises, in particular, pumping means 54 to make the blood flow in the circuit 42 and means for monitoring certain parameters of the circuit 42, in particular, load sensors 56 which engage with the sections 46 to monitor the pressure in the pipes 44 of the circuit 42.

The cassette 48 is made, for example, by moulding, of polycarbonate or polypropylene or from another suitable material.

In the rest of the description, only a single section 46 will be described.

Figure 6:
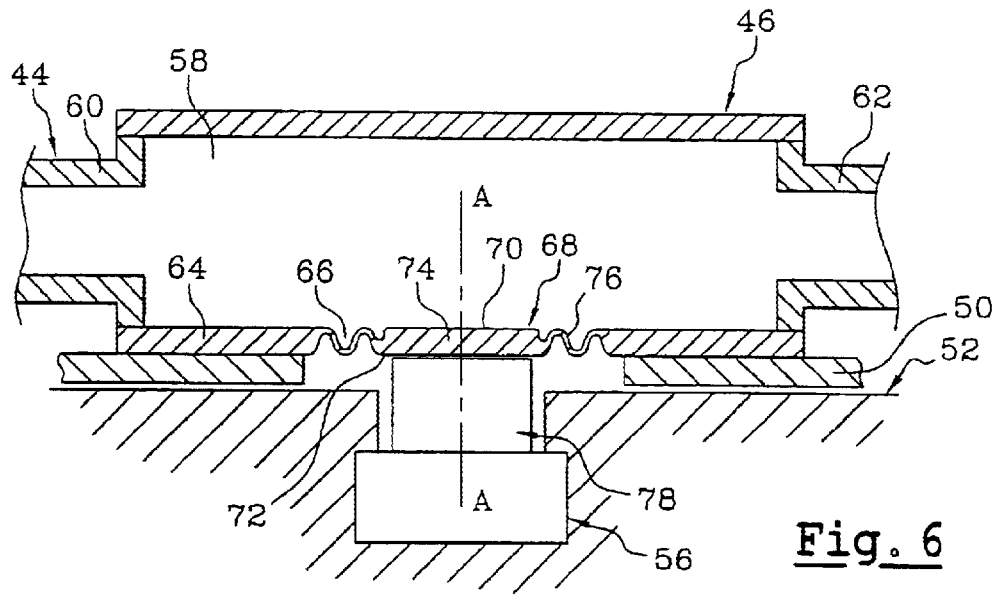
FIG. 6 is a view similar to that of FIG. 1 which shows a pressure measurement section of the device of FIG. 4.

The pressure measurement section 46, which is shown schematically in FIG. 6, in this case forms a substantially parallelepipedal compartment 58 which is inserted between two branches 60, 62 of a pipe 44, and which is, for example, moulded with the cassette 48.

According to an alternative embodiment (not shown) of the pressure measurement section 46, the latter may be a module attached to the cassette 48.

A substantially rigid wall, or main wall 64, of the pressure measurement section 46 comprises a hole 66 which is sealed by a closure element 68, the internal face 70 of which is in contact with the blood and the external face 72 of which is in contact with the ambient air.

When the cassette 48 is mounted on its support plate 50, the main wall 64 of the pressure measurement section 46 is designed to be placed facing the support plate 50, so that the closure element 68 is facing a load sensor 56.

Figure 5:
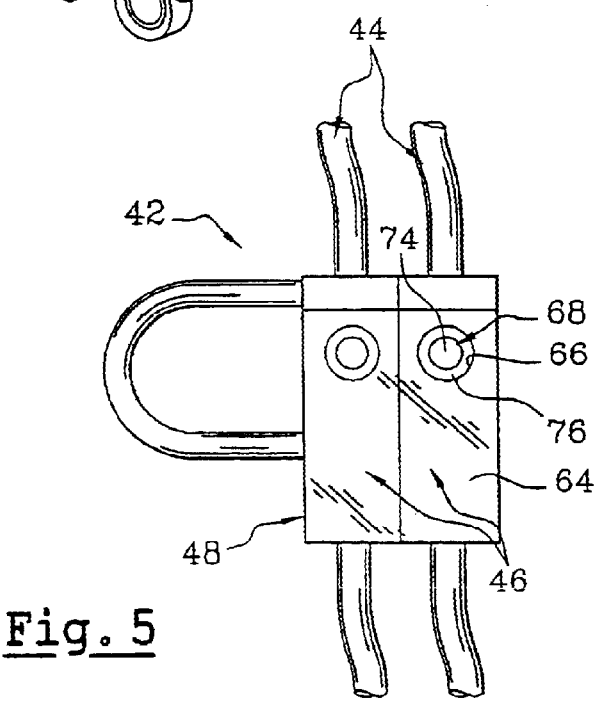
FIG. 5 is a top view which shows schematically the cassette of the device of FIG. 4.

FIG. 5 shows the cassette 48 seen from the side of the main wall 64.

In accordance with the teachings of the invention, the closure element 68 is made in a single piece with the main wall 64 of the section 46, in this case by moulding.

The closure element 68 comprises a disc-shaped substantially rigid central pellet 74 which is delimited by a thinned peripheral annular region 76 with an axial thickness less than the axial thickness of the main wall 64, so as to form an elastically deformable region.

Thus, under the effect of the pressure of the blood in the compartment 58, and by virtue of the elastic deformation of the thinned region 76, it is possible for the central pellet 74 to be displaced overall along a displacement axis A—A which is substantially orthogonal to the general plane of the pellet 74.

In its rest state, that is to say when the blood pressure is equal to the ambient air pressure, the external face 72 of the pellet 74 is in contact with a load transmitter 78 which is inserted between the pellet 74 and the load sensor 56.

The load sensor 56 may therefore measure the force applied axially to the internal face 70 of the pellet 74 by the blood pressure, in order to calculate therefrom the value of this pressure.

According to an alternative embodiment (not shown) of the closure element 68 according to the invention, the central pellet 74 has the same thickness as the thinned region 76, such that it is also elastically deformable along the axis A—A.

Preferably, the measurement section 46 is axially positioned with respect to the load transmitter 78 such that the load transmitter 78 applies an initial pretensioning force $F_0$, in the absence of a pressure gradient between the internal face 70 and the external face 72 of the closure element 68, so that contact between the closure element 68 and the load transmitter 78 can be guaranteed.

Note that, in order to make the operation of the load sensor 56 reliable, the main wall 64 of the pressure measurement section 46, which borders the hole 66, bears axially towards the outside against the support plate 50, such that, in the case of positive pressure, the main wall 64 cannot be axially deformed towards the outside.

Advantageously, as is shown in FIG. 6, in cross section on a plane which is substantially perpendicular to the general plane of the pellet 74, the profile of the thinned region 76 is substantially undulating.

The axial thickness of the thinned region 76 must, in this case, be compatible with the injection-moulding technique which makes it possible to produce the cassette 48 by moulding. This axial thickness is, for example, about 0.2 millimeters.

One advantage of the closure element 68 according to the invention is that its elasticity varies very little over time.

The effect of temperature on the elasticity of this closure element 68 is about three percent for every 10 degrees Celsius.

These small variations in elasticity may be corrected, for example, by a process of automatic correction of the measurements made by the load sensor 56.

It is found that the active surface area $S_a$ of the closure element 68 according to the invention is slightly greater than the area of contact between the pellet 74 and the load transmitter 78.

This active surface area $S_a$ depends, in particular, on the geometry of the thinned region 76.

Advantageously, the load sensor 56 is of the strain gauge type.

According to an alternative embodiment (not shown) of the invention, the thinned region 76 is made by machining the main wall 64.

The closure element 68 according to the invention makes it possible to measure positive pressure in a way similar to a conventional closure element of the flexible-membrane type.

In order to measure negative pressures, the operating principle is similar to that which is used to measure positive pressures, but a larger initial pretensioning force $F_0$ is applied so that the resultant force measured by the load sensor 56 is always positive, within the range of pressures measured.

Thus, when the pressure decreases in the compartment 58, the force measured by the load sensor 56 decreases and the value of the corresponding pressure reduction is calculated therefrom.

Note that, by choosing a suitable pretensioning force $F_0$, it is possible for the load sensor 56 to measure both positive pressures and negative pressures.

This principle of measuring a negative pressure is possible only if the pretensioning force $F_0$ does not vary during operation, or if it is possible to dynamically correct the variation in the pretensioning force $F_0$ as a function of the temperature or the creep, if there is any.

Figure 7:
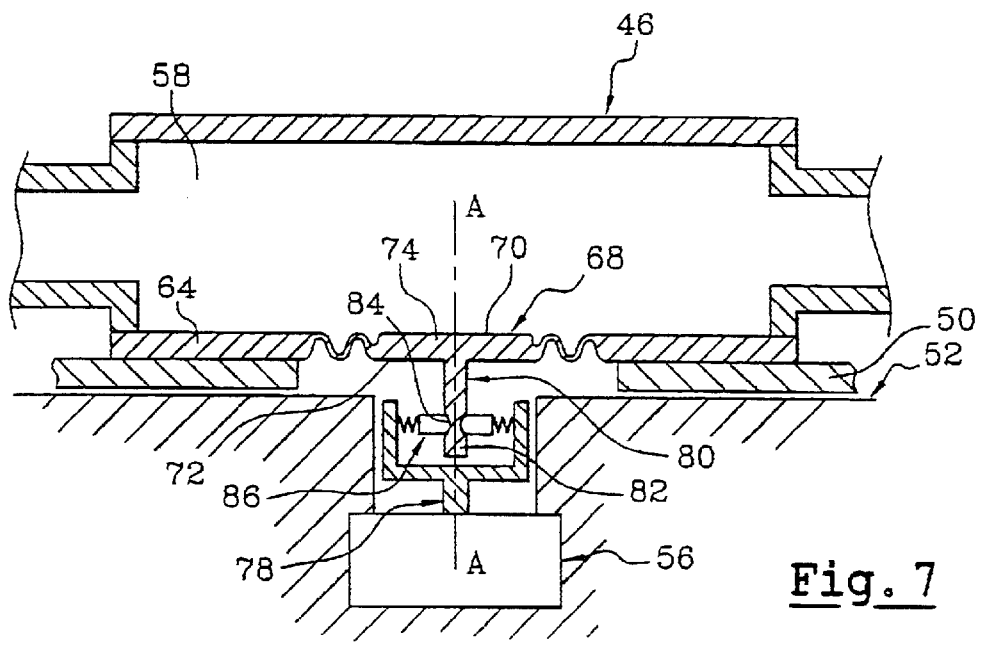
FIG. 7 is a view similar to that of FIG. 1 which shows a variant of the pressure measurement section of FIG. 6 for the purpose of measuring negative pressure.

FIG. 7 shows an alternative embodiment of the invention which makes it possible to measure negative pressures without applying a large pretensioning force $F_0$.

According to this alternative embodiment, a member 80 which can be gripped, is moulded into the external face 72 of the central pellet 74.

FIG. 7 shows schematically, by way of example, a member 80 which can be gripped and which comprises an axial rod 82 equipped with transverse notches 84.

The notches 84 engage with complementary jaws 86 of the load transmitter 78, so as to secure the pellet 74 in axial displacement with the load transmitter 78.

Thus, when the blood pressure inside the compartment 58 becomes less than the pressure of the ambient air, the central pellet 74 tends to be displaced axially towards the inside of the compartment 58, under the effect of atmospheric pressure.

The central pellet 74 therefore exerts an axial pulling force on the load transmitter 78, which makes it possible for the load sensor 56 to measure a force which corresponds to the drop in blood pressure inside the compartment 58.

Note that this alternative embodiment makes it possible to measure any pressure drop, with respect to a reference pressure, even if the blood pressure remains greater than atmospheric pressure.

What is claimed is:

1. Device for measuring the pressure of blood in a pipe of an extracorporeal blood circuit, the device comprising:

a pressure measurement section having a substantially rigid wall including a hole which is sealed by a closure element;

said closure element extending along a general plane, and having an internal face which is in contact with the blood, and an external face which is in contact with ambient air;

said closure element structured and arranged to be elastically deformed along a deformation axis which is substantially orthogonal to the general plane, under the effect of the blood pressure;

said pressure measurement section structured and arranged to engage with a load sensor so that a portion of the external face of the closure element is, in a rest state, in direct or indirect contact with the load sensor for measuring the force applied axially on the internal face of the closure element by the blood pressure, in order to calculate therefrom the value of said pressure; and said closure element being made in a single piece with the associated rigid wall of the pressure measurement section.

2. The device according to claim 1, wherein the closure element includes a region of lower resistance to elastic axial deformation, compared to the rigid wall.

3. The device according to claim 2, wherein the region of lower resistance to elastic axial deformation circumscribes the portion of the external face of the closure element.

4. The device according to claim 1, wherein the closure element comprises a substantially rigid central pellet which is delimited by a thinned peripheral annular region of axial thickness less than the axial thickness of the rigid wall in order to form an elastically deformable region.

5. The device according to claim 4, wherein the thinned peripheral annular region is made by machining the rigid wall associated with the closure element.

6. The device according to claim 1, wherein the closure element is made by molding with the associated rigid wall.

7. The device according to claim 4, wherein the profile of the peripheral annular thinned region is substantially undulating in cross section on a plane which is substantially perpendicular to the general plane of the closure element.

8. The device according to claim 4, further comprising a load transmitter inserted axially between the external face of the closure element and the load sensor.

9. The device according to claim 8, wherein the load sensor, or the load transmitter, applies an initial axial pretensioning force to the closure element, in its rest state, to measure a pressure less than the pressure of the ambient air or to measure a reduction in pressure with respect to a reference pressure.

10. The device according to claim 8, wherein the external face of the closure element comprises a gripping member which engages with a complementary member of the load transmitter, so as to secure the closure element in axial displacement with the load transmitter to measure a pressure less than the pressure of the ambient air or to measure a reduction in pressure with respect to a reference pressure.

11. The device according to claim 10, wherein the gripping member is made in a single piece with the pellet.

12. The device according to claim 1, wherein a part of the circuit is made up of a casing incorporating pipes which are connected to the extracorporeal blood circuit, and the pressure measurement section is an attached module which is mounted in an associated housing of the casing.

13. The device according to claim 10, wherein a part of the circuit is made from a casing incorporating pipes which are connected to the extracorporeal blood circuit, and the pressure measurement section is molded into the casing.

14. The device according to claim 1, wherein the closure element is substantially disc-shaped.

15. The device according to claim 1, wherein at least one portion of the rigid wall bordering the hole bears axially towards the outside against a support plate.

16. The device according to claim 1, further comprising a load transmitter inserted axially between the external face of the closure element and the load sensor.

* * * * *